(12) United States Patent
Liu et al.

(10) Patent No.: US 11,414,682 B2
(45) Date of Patent: Aug. 16, 2022

(54) MICROBIAL FERMENTATION OF BOTANICALS

(71) Applicant: CHANGSHA OMICS BIO-TECH CO. LTD, Hunan (CN)

(72) Inventors: Dongbo Liu, Hunan (CN); Lei Wang, Hunan (CN); Xincong Kang, Hunan (CN); Si Zhang, Hunan (CN); Xihu Lai, Hunan (CN)

(73) Assignee: CHANGSHA OMICS BIO-TECH CO. LTD, Hunan (CN)

( * ) Notice: Subject to any disclaimer, the term of this patent is extended or adjusted under 35 U.S.C. 154(b) by 576 days.

(21) Appl. No.: 16/096,059

(22) PCT Filed: Apr. 27, 2017

(86) PCT No.: PCT/CN2017/082207
§ 371 (c)(1),
(2) Date: Oct. 24, 2018

(87) PCT Pub. No.: WO2017/186144
PCT Pub. Date: Nov. 2, 2017

(65) Prior Publication Data
US 2019/0127763 A1    May 2, 2019

(30) Foreign Application Priority Data
Apr. 29, 2016 (CN) .......................... 201610281887.5

(51) Int. Cl.
*C12P 1/02* (2006.01)
*C12P 1/04* (2006.01)
*A61K 36/258* (2006.01)
*A61K 36/488* (2006.01)
*C12P 39/00* (2006.01)

(52) U.S. Cl.
CPC .............. *C12P 1/02* (2013.01); *A61K 36/258* (2013.01); *A61K 36/488* (2013.01); *C12P 1/04* (2013.01); *A61K 2236/19* (2013.01); *C12P 39/00* (2013.01)

(58) Field of Classification Search
None
See application file for complete search history.

(56) References Cited

U.S. PATENT DOCUMENTS

| 2010/0316763 | A1* | 12/2010 | Choi | A23L 19/00 426/18 |
| 2011/0206721 | A1* | 8/2011 | Nair | A61K 36/67 424/195.15 |
| 2016/0199424 | A1* | 7/2016 | Berry | A61K 35/747 424/93.3 |

OTHER PUBLICATIONS

Xiaoke, Ma et al. Vinegar beverage fermentation from Pueraria lobata (Willd.) Ohwi with multi-strains. Department of Journal of Jiangsu University. Natural Science Edition, vol. 35, No. 6. pp. 667-673. (Year: 2014).*

Kassim, El-Sayed. Cellulase Enzyme from Aspergillus niger. Microbiology Immunology. vol. 26 (6), pp. 449-454. (Year: 1982).*

Wang, Xing-min et al. Microbial Fermentation for Cell Disruption in Combination with Ultrasonic Treatment for the Extraction of Total Flavonoids from Pueraria lobata Tubers. vol. 32, No. 02. (Year: 2011).*

* cited by examiner

*Primary Examiner* — Nghi V Nguyen

(57) ABSTRACT

A method for microbial fermentation of botanicals includes steps of: fermenting with wall-breaking fungi, and then fermenting with probiotics. The wall-breaking fungi are wood-grown fungi and/or *Cordyceps*. The method can effectively destroy the cell wall of the botanical, promote release of effective ingredients of the botanical and improve utilization rate of the botanical. In addition, due to fermenting with the wall-breaking fungi, the botanical medicine also contains the active ingredients of the wall-breaking fungi. Thereby the efficacy of the botanical is increased.

3 Claims, No Drawings

MICROBIAL FERMENTATION OF BOTANICALS

CROSS REFERENCE OF RELATED APPLICATION

This is a U.S. National Stage under 35 U.S.C 371 of the International Application PCT/CN2017/082207, filed Apr. 27, 2017, which claims priority under 35 U.S.C. 119(a-d) to CN 201610281887.5, filed Apr. 29, 2016.

BACKGROUND OF THE PRESENT INVENTION

Field of Invention

The present invention relates to a technical field of botanical fermentation, and more particularly to a method for directionally fermenting botanicals with microorganisms, so as to promote release of active ingredients and/or increase efficacy of the botanicals.

Description of Related Arts

Natural botanicals, especially traditional Chinese medicines, have advantages in many aspects of health care and treatment compared with chemical medicines, thus being more and more widespread. However, the utilization rate of active ingredients has always been a problem. The traditional decoction method is limited because the active ingredients of botanicals is difficult to release by decoction due to the hard plant cell wall, and conventional cultivation techniques of traditional Chinese medicine also face the problems of low content of active ingredients, heavy metal pollution, and pesticide residues in botanicals, while the efficacy is also far from that of wild botanicals. Therefore, there is an urgent need for a safe and efficient process for promoting the release of active ingredients of botanicals in the field.

SUMMARY OF THE PRESENT INVENTION

The present invention provides a safe and efficient method for promoting release of active ingredients of botanicals, comprising steps of: fermenting with cell wall-breaking fungi, and then fermenting with probiotics for once or more times. The method of the present invention can effectively destroy cell walls of botanicals, so as to promote the release of the active ingredients and improve the utilization rate of botanicals.

The term "botanical" as used herein mainly refers to stems, leaves, roots, and/or fruits of a plant, which is used as a medicinal material of traditional Chinese medicine. Preferably, the botanical herein is a botanical listed in Chinese Pharmacopoeia or pharmacopoeias of other nations. In an embodiment, the botanical herein is ginseng or pueraria. It is known that ginseng belongs to *Panax*, Araliaceae, Umbellales, Dicotyledoneae; and pueraria belongs to *Pueraria*, Leguminaceae, Rosales, Magnoliopsida. It can be seen that ginseng and pueraria are very different species. The method can be applied to ginseng and pueraria, which indicates that the method of the present invention has a wide application range and can be applied to a plurality of different botanicals.

The term "wall-breaking fungus" as used herein refers to an edible fungus that has a wall-breaking effect on a hard surface structure such as a plant cell wall or an insect body wall. The wall-breaking effect mentioned here does not require the wall to be completely broken. As long as a hole is formed on the wall, the inclusions are more easily released outwards. The wall-breaking fungi include medicinal fungi, such as the multicellular fungi listed in the pharmacopoeias of each country. In the embodiment, the wall-breaking fungus is a large fungus capable of producing a fruiting body visible to the naked eye.

Main components of the plant cell walls are known to be cellulose, hemicellulose and pectin. Accordingly, edible fungi capable of producing cellulase, hemicellulase, and/or pectin are able to break the plant cell walls as described herein and therefore belong to the cell wall-breaking fungi described herein.

In fact, many edible fungi can grow on wood, such as trees. They can break through a hard wood surface and stick to it, indicating that they all have cell wall-breaking effects described herein. Therefore, these multicellular fungi growing on wood (abbreviated as "wood-grown fungi") are the cell wall-breaking fungi described herein, such as *Ganoderma, Poria cocos, Grifola umbellata*, and the like.

In addition to plant cells such as trees which have the hard surfaces, insects and larvae also have hard cellulose and chitin in body walls. Some fungi can infect larvae or pupa of insects (such as Lepidoptera), causing insects that are supposed to go through growth stages of larvae, pupa and adult to terminate at the stage of larvae or pupa. Such fungi use insect larvae or pupa as nutrition for growth, and *Cordyceps* is such a fungus. *Cordyceps* described herein refers to *Cordyceps* fungi in a broad sense, which parasitize insects, turn a caterpillar into a dead one filled with hyphae, and produce a stem-like or stick-like stroma from the front end of the caterpillars. *Cordyceps* fungi have been reported in more than 500 species, the most widely known of which are *Cordyceps sinensis, Cordyceps militaris* and the like. *Cordyceps* can break through the body wall of insects, indicating that it can produce corresponding wall-breaking substances such as cellulase, chitinase, etc., and therefore belongs to the wall-breaking fungi described herein.

Accordingly, in the embodiment, the wall-breaking fungi described herein comprise the wood-grown fungi and *Cordyceps*. In a preferred embodiment, the wall-breaking fungus described herein is selected from the group consisting of *Ganoderma, Poria cocos, Grifola umbellata*, and/or *Cordyceps militaris*.

The term "fermentation" herein is a process in which microorganisms are inoculated in plants or fruits, stems, leaves or the like. Due to life activities of microorganisms, carbohydrates can be converted into substances such as alcohols and organic acids, and components (such as nutrients) contained in plants can be changed. For example, components in plants could be more easily released, be more active, or become more absorbable to the human body.

The term "ferment nutrients" herein refers to a mixture of a plurality of biologically active substances obtained by fermenting plants with probiotics, comprising: fermentation-participating microorganisms, edible materials for fermentation, active ingredients of the fermentation-participating microorganisms or the edible materials such as a plurality types of enzymes. The ferment nutrients further comprise ingredients that are improved by fermentation, such as ingredients that are more active or more absorbable, and the like.

The term "probiotics" as used herein refers to microorganisms in the human body that are beneficial to health. Probiotics are often used to make foods such as yogurt and ferment nutrients. Commonly used probiotics comprise yeast, *Lactobacillus, Bifidobacterium, Leuconostoc, Streptococcus, Lactococcus, Acetobacterium*, etc. The yeast comprises *Saccharomyces* such as *Saccharomyces cerevisiae* and *Saccharomyes eerevisiae, Pichia* such as *Pichia pastoris, Pichia ohmeri* and *Pichia membranaefaciens*, and *Hansenula* such as *Hansenula anomala*. The *Lactobacillus* comprises *Lactobacillus buchneri, Lactobacillus panis, Lactobacillus acidophilus, Lactobacillus plantarum, Lactobacillus fermenti, Lactobacillus salivarius, Lactobacillus brevis, Lactobacillus veridescens, Lactobacillus delbrueckii bulgaricus, Lactobacillus rhamnosus, Lactobacillus cellobiosus, Lactobacillus casei* subsp. *casei, Lactobacillus helveticus* subsp. *jugurti, Lacticum jansen, Lactobacillus pentosus* and so on. The *Bifidobacterium* comprises *Bifidobacterium adolescents, Bifidobacterium bifidum, Bifidobacterium infantis, Bifidobacterium longum*, and the like. The *Acetobacterium* comprises *Acetobacter pasteuranus, Acetobacter rancens*, and the like. Other probiotics comprises: *Leuconostoc mesenteroides aureus, Streptococcus salivarius* subsp. *thermophilus, Lactococcus lactis* subsp. *Cremoris*, and the like.

The applicant has found that the contents of botanical active ingredients are greatly improved in the fermentation broth of different botanicals fermented by wall-breaking fungi and probiotics by compared with those of traditional decoction soups. Thereby the fermentation method could improve the current administration methods of traditional Chinese medicines and solve the problem of low efficacy of traditional Chinese medicine under current cultivation methods. Botanical fermented product, which obtained by the method of the present invention, comprises botanical active ingredients and various active enzymes or active substances derived from the wall-breaking fungi and probiotics. The botanical fermented product is a nutrient-rich preparation that can be used to condition human health.

Accordingly, the present invention also relates to a fermentation method which combines wall-breaking fungus fermentation with probiotic fermentation. The fermentation method may be a fermentation method of botanicals. In the embodiment, the present invention refers to the fermentation with the wall-breaking fungi and then with the probiotics. In the embodiment, the probiotic fermentation of the present invention uses yeast, *Lactobacillus*, and *Acetobacterium*. In the embodiment, the probiotic fermentation of the present invention is carried out in a stepwise manner, for example, a mixed fermentation of yeast and *Lactobacillus* is followed by fermentation of *Acetobacterium*. Both the wall-breaking fungus fermentation and the probiotic fermentation are performed under the culture conditions (e.g. temperature, pH) applicable to each strains, which are known to those skilled in the art.

Culture mediums of the wall-breaking fungus such as *Ganoderma* and *Cordyceps* are also common in the art. For example, one medium comprises (by mass ratio): glucose 1-6%, yeast extract 0.1%-0.4%, peptone 0.1%-0.8%, potassium dihydrogen phosphate 0.05%-0.3%, magnesium sulfate 0.05%-0.3%, and water. Glucose as a carbon source can be replaced with potato juice, and other ingredients can be adjusted. Such adjustments are common to those skilled in the art. In the embodiment of the present invention, in order to unify an experimental system, the following compositions (by mass ratio) are used: glucose 2.4%, yeast extract 0.2%, peptone 0.4%, potassium dihydrogen phosphate 0.1%, magnesium sulfate 0.1%, and distilled water 96.8%.

In a preferred embodiment, the wall-breaking fungi, which can share the same or similar culture conditions, can also be cultured together in the same medium. Optionally, probiotic fermentation is further performed, such that the final product contains more than one type of wall-breaking fungus and/or active ingredients thereof.

Fermentation of the wall-breaking fungi was under the conditions of stirring at 50-250 rpm, 7-30° C. for 3-45 days. These conditions are known to those skilled in the art based on the growth requirements of specific species of the wall-breaking fungi.

The probiotic fermentation may be sealed and static, fermented at 10-40° C. for more than 48 h. In the embodiment, each probiotic of the present invention adopts a bacterial liquid having millions of viable bacteria, which is inoculated in an amount of 1-3‰ mass fraction of a total raw material. These conditions are also known to those skilled in the art based on the growth requirements of specific species of the probiotics.

Preferably, the fermentation process of the present invention does not involve a step of extracting the active ingredients of the wall-breaking fungi. That is to say, the method does not require extraction of a large number of fungal active ingredients before or after the wall-breaking fungus fermentation, and fermentation of the wall-breaking fungi and the probiotics can be carried out sequentially in the same culture system or fermentation device.

In the embodiment, the method of the present invention comprises steps of:

1) selecting botanical fresh medicinal materials and botanical medicine pieces that meet requirements, crushing to 10-30 meshes, pouring into a fermenting tank, adding 5-20 times (mass) culture solution, stirring for thoroughly mixing;

2) adjust pH to 5.0-8.0 with vinegar or sodium hydroxide solution, and then sterilizing with steam for 30-60 min;

3) cooling to room temperature, and inoculating a medicinal fungus, keeping a stirring speed of the fermentation tank at 50-250 rpm, keeping a temperature at 7-30° C., and fermenting for 3-45 days to complete the first fermentation;

4) then inoculating the probiotic, sealing and statically culturing at 10-40° C. for more than 48 h to complete the second fermentation; and 5) filtering out dregs and collecting fermentation broth.

The present invention has advantages that the fermentation method, that fermented the botanical with the wall-breaking fungi firstly and then fermented by inoculating the probiotics (or more times), can effectively destroy the cell wall of the botanical, promote release of effective ingredients of the botanical and improve utilization rate of the botanical. In addition, due to fermenting with the wall-breaking fungi, the botanical medicine liqid also contains the active ingredients of the wall-breaking fungi. Thereby the efficacy of the botanical is increased.

Preferably, the present application relates to:

1. A microbial fermentation method of botanicals, comprising steps of: fermenting with wall-breaking fungi, and then fermenting with probiotics.

2. The microbial fermentation method, as recited in point 1, wherein the wall-breaking fungus is a wood-grown fungus and/or a *Cordyceps*.

3. The microbial fermentation method, as recited in point 1 or 2, wherein the wall-breaking fungi are selected from a group consisting of *Ganoderma, Grifola umbellata, Poria cocos, Cordyceps sinensis* and/or *Cordyceps militaris*.

4. The microbial fermentation method, as recited in point 1, 2 or 3, wherein the probiotics are selected from a group consisting of *Saccharomyces, Pichia, Hansenula, Lactobacillus, Bifidobacterium, Leuconostoc, Streptococcus, Lactococcus* and *Acetobacterium*.

5. The microbial fermentation method, as recited in point 4, wherein the probiotics are selected from a group consisting of Saccharomyces cerevisiae, Saccharomyes eerevisiae, Pichia pastoris, Pichia ohmeri, Pichia membranaefaciens, Hansenula anomala, Lactobacillus buchneri, Lactobacillus panis, Lactobacillus acidophilus, Lactobacillus plantarum, Lactobacillus fermenti, Lactobacillus salivarius, Lactobacillus brevis, Lactobacillus veridescens, Lactobacillus delbrueckii bulgaricus, Lactobacillus rhamnosus, Lactobacillus cellobiosus, Lactobacillus casei subsp. casei, Lactobacillus helveticus subsp. jugurti, Lacticum jansen, Lactobacillus pentosus, Acetobacter pasteuranus, Acetobacter rancens, Bifidobacterium adolescents, Bifidobacterium bifidum, Bifidobacterium infantis, Bifidobacterium longum, Leuconostoc mesenteroides aureus, Streptococcus salivarius subsp. thermophilus and Lactococcus lactis subsp. Cremoris.

6. The microbial fermentation method, as recited in point 5, wherein the probiotics comprise yeast, Lactobacillus and Acetobacterium.

7. The microbial fermentation method, as recited in point 6, wherein mixed fermentation of yeast and Lactobacillus is followed by fermentation of Acetobacterium.

8. The microbial fermentation method, as recited in points 1-7, wherein the botanical is ginseng.

9. The microbial fermentation method, as recited in points 1-7, wherein the botanical is pueraria.

10. A product prepared by the microbial fermentation method of botanicals as recited in points 1-9.

DETAILED DESCRIPTION OF THE PREFERRED EMBODIMENT

The following embodiments are intended to describe the present invention in detail, and are not intended to limit the scope of the present invention. Modifications and adjustments made by those skilled in the art based on the disclosure also belong to the scope of the present invention.

Embodiment 1

Weighing 10 Kg of ginseng, pulverizing to 30 meshes, pouring into a fermenting tank, adding 80 Kg of culture solution (by mass ratio: glucose 2.4%, yeast extract 0.2%, peptone 0.4%, potassium dihydrogen phosphate 0.1%, magnesium sulfate 0.1%, and distilled water 96.8%), thoroughly mixing, adjusting pH to 6.8 with sodium hydroxide solution, sterilizing with steam for 30 min; cooling to room temperature, and inoculating Ganoderma lucidum (Xiangchizhi No. 1, Hunan Province non-major crop variety registration certificate number XPD010-2013, obtained from State Key Laboratory of Sub-health Intervention Technology), keeping a stirring speed in the fermentation tank at 120 rpm, keeping the temperature at 20° C., and fermenting for 15 days; then adding 1‰ (total raw material mass fraction) yeast (Pichia ohmeri, CGMCC No. 2.1803, millions of viable bacteria) and 1‰ (total raw material mass fraction) Lactobacillus (Lactobacillus plantarum, CGMCC No. 1.6971, millions of viable bacteria), and statically fermenting at 28° C. for 7 days; then adding 1‰ (total raw material mass fraction) Acetobacterium (Acetobacter pasteuranus CGMCC No. 1.41, purchased from Shanghai No. 1 Brewing Plant, millions of viable bacteria), statically fermenting at 30° C. for 7 days; filtering and collecting liquid.

According to test, the ginseng liquid obtained by the present invention has a total ginsenoside content of 1.06 mg/mL (the determination method refers to that in the paper of "Content determination of total ginsenoside, Gao Liping et al., Journal of Zhejiang Institute of Engineering, 2012, 31(3): 382-388"), which is 7.01 times higher than the conventional decoction (a weight ratio of ginseng and water is 1:8). Furthermore, 0.75 mg/mL Ganoderma triterpenoid content is also detected in the liquid (the assay method refers to that in "Chinese Pharmacopoeia 2015 edition"). All data are average values of triplicate samples.

Embodiment 2

Weighing 10 Kg of ginseng, pulverizing to 30 meshes, pouring into a fermenting tank, adding 80 Kg of the culture solution as mentioned in the embodiment 1, thoroughly mixing, adjusting pH to 6.8 with sodium hydroxide solution, sterilizing with steam for 30 min; cooling to room temperature, and inoculating Ganoderma (Ganoderma tsugae, CGMCC No. 5.772, belonging to Ganoderma sinense), keeping a stirring speed in the fermentation tank at 100 rpm, keeping temperature at 23° C., and fermenting for 15 days; then adding 1‰ (total raw material mass fraction) yeast (Saccharomyces cerevisiae, CGMCC No. 2.3888, millions of viable bacteria) and 1‰ (total raw material mass fraction) Lactobacillus (Lactobacillus panis, CGMCC No. 1.3925, millions of viable bacteria), and statically fermenting at 28° C. for 7 days; then adding 1‰ (total raw material mass fraction) Acetobacterium (Acetobacter pasteurianus CGMCC No. 1.41, millions of viable bacteria), statically fermenting at 30° C. for 7 days; filtering and collecting liquid.

According to test, the ginseng liquid obtained by the present invention has a total ginsenoside content of 1.03 mg/mL (the determination method as mentioned in the embodiment 1), which is 6.81 times higher than the conventional decoction (a weight ratio of ginseng and water is 1:8). Furthermore, 0.64 mg/mL Ganoderma triterpenoid content is also detected in the liquid (the assay method as mentioned in the embodiment 1). All data are average values of triplicate samples.

Embodiment 3

Weighing 10 Kg of pueraria, pulverizing to 20 meshes, pouring into a fermenting tank, adding 100 Kg of culture solution as mentioned in the embodiment 1, thoroughly mixing, adjusting pH to 6.5 with sodium hydroxide solution, sterilizing at 121° C. for 30 min; cooling to room temperature, and inoculating Cordyceps (Xiangbeichongcao No. 1, Hunan Province non-major crop variety registration certificate number XPD009-2013, obtained from State Key Laboratory of Sub-health Intervention Technology), keeping a stirring speed in the fermentation tank at 150 rpm, keeping temperature at 25° C., and fermenting for 10 days; then adding 3‰ (total raw material mass fraction) yeast (Saccharomyces cerevisiae, CGMCC No. 2.3973, millions of viable bacteria) and 1‰ (total raw material mass fraction) Lactobacillus (Lactobacillus buchneri, CGMCC No. 1.3114, millions of viable bacteria), and statically fermenting at 28° C. for 8 days; then adding 1‰ (total raw material mass fraction) Acetobacterium (Acetobacter pasteuranus SHBCC D24822, millions of viable bacteria), statically fermenting at 30° C. for 7 days; filtering and collecting liquid.

According to test, the pueraria liquid obtained by the present invention has a puerarin content of 0.119 mg/mL (the determination method refers to that in "Health Foods of Chinese National Standard GB/T 22251-2008"), which is 1.25 times higher than the conventional decoction (a weight ratio of pueraria and water is 1:10). Furthermore, 11.3 µg/mL cordycepin content is also detected in the liquid (the assay method refers to that in "Screening of high yield strains of cordycepin and effects of different additives on the yield of cordycepin, Wang Lei et al., Journal of Fungal Materials, 2012, 31(3): 382-388"). All data are average values of triplicate samples.

Embodiment 4

Weighing 10 Kg of pueraria, pulverizing to 20 meshes, pouring into a fermenting tank, adding 100 Kg of the culture solution as mentioned in the embodiment 1, thoroughly mixing, adjusting pH to 6.5 with sodium hydroxide solution, sterilizing at 121° C. for 30 min; cooling to room temperature, and inoculating Cordyceps (Cordyceps militaris, CGMCC No. 5.856), keeping a stirring speed in the fermentation tank at 130 rpm, keeping temperature at 28° C., and fermenting for 10 days; then adding 3‰ (total raw material mass fraction) yeast (Pichia membranaefaciens, CGMCC No. 2.661, millions of viable bacteria) and 1‰ (total raw material mass fraction) Lactobacillus (Lactobacillus panis, CGMCC No. 1.3925, millions of viable bacteria), and tatically fermenting at 28° C. for 8 days; then adding 1‰ (total raw material mass fraction) Acetobacterium (Acetobacterium Huniang 1.01, millions of viable bacteria), statically fermenting at 30° C. for 7 days; filtering and collecting liquid.

According to test, the pueraria liquid obtained by the present invention has a puerarin content of 0.113 mg/mL (the determination method as mentioned in the embodiment 3), which is 1.19 times higher than the conventional decoction (a weight ratio of pueraria and water is 1:10). Furthermore, 13.7 µg/mL cordycepin content is also detected in the liquid (the assay method as mentioned in the embodiment 3). All data are average values of triplicate samples.

The following biological materials are readily accessible to the public, and have been deposited under the terms of the Budapest Treaty with the China General Microbiological Culture Collection Center (CGMCC), Institute of Microbiology, Chinese Academy of Sciences, Haidian, Beijing 100080, China:

(1) Name: *Pichia ohmeri*
Accession Number: CGMCC No. 2.1803
Date of Deposit: 1994 Oct. 1
Classification: *Ascomycota*.genus, *Pichia* sp, *P. ohmeri*
Origin: China (2) Name: *Lactobacillus plantarum*
Accession Number: CGMCC No. 1.6971
Date of Deposit: 2007 Jul. 1
Classification: Bacteria, Firmicutes, Bacilli, Lactobacillales, Lactobacillaceae, *Lactobacillus*
Origin: China (3) Name: *Acetobacter pasteurianus*
Accession Number: CGMCC No. 1.41
Date of Deposit: 1950 Dec. 1
Classification: Proteobacteria, *Acetobacter, Acetobacter pasteurianus*
Origin: China (4) Name: *Ganoderma tsugae*
Accession Number: CGMCC No. 5772
Date of Deposit: 1999 Jun. 22
Classification: Basidiomyceta, Lamella, Pales, Poramellaceae, *Ganoderma*
Origin: Holland (5) Name: *Saccharomyces cerevisiae*
Accession Number: CGMCC No. 2.3888
Date of Deposit: Publicly available
Classification: Eukarya, Fungi, Ascomycota, Hemiascomycete, Saccharomycetales, Saccharomycetaceae, *Saccharomyces, S. cerevisiae*
Origin: China (6) Name: *Lactobacillus panis*
Accession Number: CGMCC No. 1.3925
Date of Deposit: 2005 Apr. 25
Classification: Bacterium, Firmicutes, *Bacillus, Lactobacillus*, Lactobacillaceae, *Lactobacillus panis*
Origin: China (7) Name: *Saccharomyces cerevisiae*
Accession Number: CGMCC No. 2.3973
Date of Deposit: 2008, Sep. 16
Classification: Eukarya, Fungi, Ascomycota, Hemiascomycete, Saccharomycetales, Saccharomycetaceae, *Saccharomyces, S. cerevisiae*
Origin: China (8) Name: *Lactobacillus buchneri*
Accession Number: CGMCC No. 1.3114
Date of Deposit: 2002 Jul. 2
Classification: Bacterium, Firmicutes, *Bacillus, Lactobacillus*, Lactobacillaceae, *Lactobacillus buchneri*
Origin: China The following biological material is readily accessible to the public, and has been deposited with the Shanghai Bioresource Collection Center (SHBCC), Fengxian, Shanghai, 201414, China:

(9) Name: *Acetobacter pasteurianus*
Accession Number: SHBCC D24822
Date of Deposit: 1971 Dec. 1
Classification: Proteobacteria, *Acetobacter, Acetobacter pasteurianus*
Origin: China

What is claimed:

1. A microbial fermentation method of botanicals, comprising steps of:
weighing 10 Kg of ginseng, pulverizing to 30 meshes, pouring into a fermenting tank, adding 80 Kg of culture solution which, by mass ratio, comprises: glucose 2.4%, yeast extract 0.2%, peptone 0.4%, potassium dihydrogen phosphate 0.1%, magnesium sulfate 0.1%, and distilled water 96.8%; thoroughly mixing, adjusting pH to 6.8 with sodium hydroxide solution, sterilizing with steam for 30 min; cooling to room temperature, and inoculating *Ganoderma lucidum*, keeping a stirring speed in the fermentation tank at 120 rpm, keeping a temperature at 20° C., and fermenting for 15 days; then adding 1‰ total raw material mass fraction of yeast and 1‰ total raw material mass fraction of *Lactobacillus*, and statically fermenting at 28° C. for 7 days; then adding 1‰ total raw material mass fraction of *Acetobacterium*, statically fermenting at 30° C. for 7 days; filtering and collecting liquid;
wherein the yeast is *Pichia ohmeri*, CGMCC No. 2.1803; the *Lactobacillus* is *Lactobacillus plantarum*, CGMCC No. 1.6971, with millions of viable bacteria; and the *Acetobacterium* is *Acetobacter pasteurianus* CGMCC No. 1.41, with millions of viable bacteria.

2. A microbial fermentation method of botanicals, comprising steps of:
weighing 10 Kg of ginseng, pulverizing to 30 meshes, pouring into a fermenting tank, adding 80 Kg of culture solution which, by mass ratio, comprises: glucose 2.4%, yeast extract 0.2%, peptone 0.4%, potassium dihydrogen phosphate 0.1%, magnesium sulfate 0.1%, and distilled water 96.8%; thoroughly mixing, adjusting pH to 6.8 with sodium hydroxide solution, sterilizing with steam for 30 min; cooling to room temperature, and inoculating *Ganoderma*, keeping a stirring speed in the fermentation tank at 100 rpm, keeping a temperature at 23° C., and fermenting for 15 days; then adding 1‰ total raw material mass fraction of yeast and 1‰ total raw material mass fraction of *Lactobacillus*, and statically fermenting at 28° C. for 7 days; then adding 1‰ total raw material mass fraction of *Acetobacterium*, statically fermenting at 30° C. for 7 days; filtering and collecting liquid;

wherein the *Ganoderma* is *Ganoderma tsugae*, CGMCC No. 5.772; the yeast is *Saccharomyces cerevisiae*, CGMCC No. 2.3888; the *Lactobacillus* is *Lactobacillus panis*, CGMCC No. 1.3925, with millions of viable bacteria; and the *Acetobacterium* is *Acetobacter pasteurianus* CGMCC No. 1.41, with millions of viable bacteria.

3. A microbial fermentation method of botanicals, comprising steps of:

weighing 10 Kg of pueraria, pulverizing to 20 meshes, pouring into a fermenting tank, adding 100 Kg of culture solution which, by mass ratio, comprises: glucose 2.4%, yeast extract 0.2%, peptone 0.4%, potassium dihydrogen phosphate 0.1%, magnesium sulfate 0.1%, and distilled water 96.8%; thoroughly mixing, adjusting pH to 6.5 with sodium hydroxide solution, sterilizing at 121° C. for 30 min; cooling to room temperature, and inoculating *Cordyceps*, keeping a stirring speed in the fermentation tank at 150 rpm, keeping a temperature at 25° C., and fermenting for 10 days; then adding 3% total raw material mass fraction of yeast and 1‰ total raw material mass fraction of *Lactobacillus*, and statically fermenting at 28° C. for 8 days; then adding 1‰ total raw material mass fraction of *Acetobacterium*, statically fermenting at 30° C. for 7 days; filtering and collecting liquid;

wherein the yeast is *Saccharomyces cerevisiae*, CGMCC No. 2.3973; the *Lactobacillus* is *Lactobacillus buchneri*, CGMCC No. 1.3114, with millions of viable bacteria; and the *Acetobacterium* is *Acetobacter pasteuranus* SHBCC D24822, with millions of viable bacteria.

* * * * *